US006635766B1

(12) United States Patent
Roduit et al.

(10) Patent No.: US 6,635,766 B1
(45) Date of Patent: *Oct. 21, 2003

(54) PROCESS FOR THE PREPARATION OF ARYLAMIDES OF HETEROAROMATIC CARBOXYLIC ACIDS

(75) Inventors: Jean-Paul Roduit, Grône (CH); Georges Kalbermatten, Ausserberg (CH)

(73) Assignee: Lonza AG, Gampel/Valais (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 996 days.

(21) Appl. No.: 08/829,512

(22) Filed: Mar. 28, 1997

(30) Foreign Application Priority Data

Mar. 28, 1996 (CH) ............................................... 0806/96

(51) Int. Cl.$^7$ ............................................. C07D 213/00
(52) U.S. Cl. ........................ 546/298; 546/301; 546/302; 544/329; 544/406
(58) Field of Search ................................ 546/300, 301, 546/302, 298; 544/329, 335, 406, 408

(56) References Cited

U.S. PATENT DOCUMENTS

| | | | |
|---|---|---|---|
| 4,128,554 A | 12/1978 | Heck | |
| 4,618,366 A | 10/1986 | Cramp et al. | |
| 4,995,902 A | 2/1991 | Brunner | |
| 5,142,057 A | 8/1992 | Suto et al. | |
| 5,159,113 A | 10/1992 | Nicholas | |
| 5,166,352 A | 11/1992 | Allphin | |
| 5,288,866 A | 2/1994 | Strong | |
| 5,294,597 A | 3/1994 | Foster et al. | |
| 5,296,601 A | 3/1994 | Suto et al. | |
| 5,334,724 A | 8/1994 | Kaufman et al. | |
| 5,380,861 A | 1/1995 | Scalone et al. | |
| 5,534,635 A | 7/1996 | Scalone et al. | |
| 5,583,241 A | 12/1996 | Spindler | |
| 5,614,636 A | 3/1997 | Roduit et al. | |
| 5,676,267 A | 10/1997 | Slat et al. | |

FOREIGN PATENT DOCUMENTS

| | | |
|---|---|---|
| CH | 0 664 754 | 3/1988 |
| DE | 42 07 604 | 10/1992 |
| EP | 0001187 | 3/1979 |
| EP | 0053011 | 6/1982 |
| EP | 0282266 | 9/1988 |
| EP | 0 353 187 | 1/1990 |
| EP | 0 582 825 | 2/1990 |
| EP | 0 488 474 | 6/1991 |
| EP | 0447004 | 9/1991 |
| EP | 0 461 401 | 11/1991 |
| EP | 0 564 406 | 10/1993 |
| EP | 0 612 758 | 8/1994 |
| EP | 0627422 | 12/1994 |
| EP | 0646590 | 4/1995 |
| EP | 0 673 932 | 9/1995 |
| WO | WO 93/18005 | 9/1993 |
| WO | WO 94/27974 | 12/1994 |

OTHER PUBLICATIONS

Journal of Organometallic Chemistry, (1995), 503, 143–148.
Inorganica Chimica Acta, (1994), 222, 213–214.
Journal of Heterocyclic Chemistry, (1990), 27, 243.
Chemical Abstracts, (1996), vol. 125, No. 3, 33323k.
Encyclopedia of Reagents for Organic Synthesis, (1995), 2769–2771.
Chemical Abstracts, (1994), vol. 122, 18621.
Chemical Abstracts, (1988), vol. 109, 68849.
Chemical Abstracts, (1969), vol. 73, 130894.
Advanced Organic Chemistry, Mar., (1968), 21.
Shokubai Catalysis Society of Japan, 36, (1994), 580–584.
Journal of Organic Chemistry, (1980), 45, 4680–4682.
Schoenberg et al., *Journal of Organic Chemistry*, vol. 39, No. 23, (1974), pp. 3327 to 3331.
Takeuchi et al., *Journal of Molecular Catalysis*, vol. 66, No. 3, (1991), pp. 277 to 288.
Ben–David et al., *Journal of American Chemical Society*, vol. 111, No. 23, (1989).
CA:109:68849 abs of JP63005005.*
CA:122:187621 abs of WO9427974.*
CA:73:130894 abs of FR1582125.*

* cited by examiner

*Primary Examiner*—Jean F. Vollano
(74) *Attorney, Agent, or Firm*—Fisher, Christen & Sabol

(57) ABSTRACT

A process for the preparation of arylamides of heteroaromatic carboxylic acids of the formula:

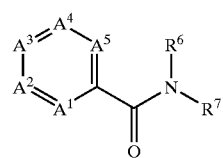

I in which each $A^n$ is nitrogen or $CR^n$ (n=1 to 5), with the proviso that at least one of the ring members is nitrogen and that two nitrogen atoms are not bonded directly to one another; $R^1$ to $R^5$, if present, independently of one another; $C_{1-4}$-alkyl or aryl, one of the substituents $R^1$ to $R^5$ being a group of the formula —OR, in which R is an optionally substituted aromatic or heteroaromatic radical; $R^6$ is hydrogen or $C_{1-4}$-alkyl; and $R^7$ is an optionally substituted aromatic or heteroaromatic radical. The amides are obtained from the corresponding heteroaromatic halogen compounds, the corresponding aromatic amines and carbon monoxide in the presence of palladium diphosphine complex. Compounds of this class (Formula I) are important herbicides.

18 Claims, No Drawings

PROCESS FOR THE PREPARATION OF ARYLAMIDES OF HETEROAROMATIC CARBOXYLIC ACIDS

SUMMARY DESCRIPTION OF THE INVENTION

The invention relates to a process for the preparation of arylamides of heteroaromatic carboxylic acids by the reaction of heteroaromatic halogen compounds with carbon monoxide and aromatic amines in the presence of a catalyst and a base. It further relates to a process for the preparation of arylamides of heteroaromatic carboxylic acids which carry an aryloxy or heteroaryloxy group as a substituent on the heteroaromatic ring, by the reaction of heteroaromatic dihalogen compounds with aromatic or heteroaromatic hydroxyl compounds to give (hetero)aryloxy-substituted heteroaromatic monohalogen compounds, and the further reaction of these compounds with carbon monoxide and aromatic amines in the presence of a catalyst and a base.

The amides which can be prepared according to the invention have the general formula:

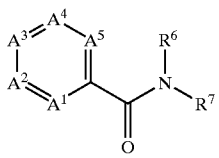

I in which:
- $A^1$ is nitrogen or $CR^1$,
- $A^2$ is nitrogen or $CR^2$,
- $A^3$ is nitrogen or $CR^3$,
- $A^4$ is nitrogen or $CR^4$, and
- $A^5$ is nitrogen or $CR^5$,
- with the proviso that at least one of the ring members $A^1$ to $A^5$ is nitrogen and that two nitrogen atoms are not bonded directly to one another;
- $R^1$ to $R^5$, if present, independently of one another are hydrogen, $C_{1-4}$-alkyl or aryl, one of the substituents $R^1$ to $R^5$ being a group of the formula —OR, in which R is an optionally substituted aromatic or heteroaromatic radical;
- $R^6$ is hydrogen or $C_{1-4}$-alkyl; and
- $R^7$ is an optionally substituted aromatic or heteroaromatic radical.

Such amides include especially the arylamides of pyridine-, pyrimidine-, pyrazine- and 1,3,5-triazine-carboxylic acids.

BACKGROUND ART

Numerous compounds of the structure of Formula 1, especially those in which one of the substituents $R^1$ to $R^5$ is an aryloxy group (—OR) adjacent to a ring nitrogen atom, are important herbicides (WO-A 94/27974, European Published Patent Application No. 0,053,011, and European Published Patent Application No. 0,447,004). These known compounds are conventionally synthesized from the corresponding carboxylic acids or carboxylic acid derivatives (acid chlorides, esters, and nitriles), although these are often difficult to obtain and, consequently, expensive.

BROAD DESCRIPTION OF THE INVENTION

The main object of the invention is to provide an alternative process which is based on more readily obtainable educts. Other objects and advantages of the invention are set out herein or are obvious herefrom to one skilled in the art. The objects and advantages of the invention are achieved by the process of the invention.

The invention involves a process for the preparation of amides of the general formula:

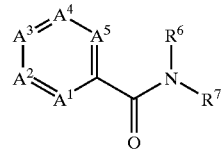

I in which
- $A^1$ is nitrogen or $CR^1$,
- $A^2$ is nitrogen or $CR^2$,
- $A^3$ is nitrogen or $CR^3$,
- $A^4$ is nitrogen or $CR^4$, and
- $A^5$ is nitrogen or $CR^5$,
- with the proviso that at least one of the ring members $A^1$ to $A^5$ is nitrogen and that two nitrogen atoms are not bonded directly to one another;
- $R^1$ to $R^5$, if present, independently of one another are hydrogen, $C_{1-4}$-alkyl or aryl, one of the substituents $R^1$ to $R^5$ being a group of the formula —OR, in which R is an optionally substituted aromatic or heteroaromatic radical;
- $R^6$ is hydrogen or $C_{1-4}$-alkyl; and
- $R^7$ is an optionally substituted aromatic or heteroaromatic radical, comprising reacting a halogen compound of the general formula:

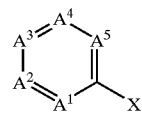

II in which $A^1$ to $A^5$ are as defined above and X is chlorine, bromine or iodine, with carbon monoxide and an amine of the general formula:

$R^6$—NH—$R^7$                III, in which $R^6$ and R7 are as defined above, in the presence of a complex of palladium with a diphosphine of the general formula:

$R^8R^9P$—$[CH_2]_n$—$PR^{10}R^{11}$                IV, in which $R^8$ to $R^{11}$ independently of one another are phenyl or substituted phenyl and n is 3 or 4, and with a base.

Preferably, in Formulae I and II, $A^2$ is nitrogen and part of a pyridine ring. Preferably, in Formulae I and II, $R^1$ is a group of the formula —OR.

Also preferably, in Formulae I and II, $A^1$ is nitrogen and part of a pyridine ring.

Also preferably, in Formulae I and II, $A^1$ and $A^5$ are nitrogen and part of a pyrimidine ring.

Also preferably, in Formulae I and II, $A^1$ and $A^4$ are nitrogen and part of a pyrazine ring.

Preferably, in Formulae I and II, $A^1$, $A^3$ and $A^5$ are nitrogen.

In each of the last four preferable embodiments listed just above, preferably, in Formulae I and II, $R^2$ is a group of the formula —OR.

Preferably, in Formulae I and II, R is an optionally substituted phenyl group, in Formulae I and III, $R^6$ is hydrogen and $R^7$ is an optionally substituted phenyl group.

Preferably, in Formula II, X is chlorine.

Preferably, the diphosphine (IV) used is 1,3-bis(diphenylphosphino)propane or 1,4-bis(diphenylphosphino)butane.

The invention also involves a process for the preparation of amides of the general formula:

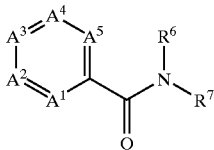

I in which $A^1$ to $A^5$, $R^6$ and $R^7$ are as defined above, comprising, in a first step, reacting a dihalide of the general formula:

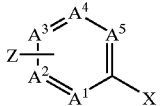

V in which $A^1$ to $A^5$ are as defined above with the proviso that one of the radicals $R^1$ to $R^5$ on a carbon atom adjacent to a ring nitrogen atom is replaced with Z, Z is chlorine, bromine or iodine and X independently thereof is chlorine, bromine or iodine, with an aromatic or heteroaromatic hydroxyl compound of the general formula:

R—OH      VI, in which R is as defined above, to give a (hetero)aryloxy halogen compound of the general formula:

II'

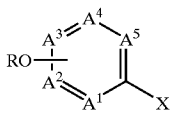

in which $A^1$ to $A^5$, and X are as defined above, and, in a second step, reacting said product with carbon monoxide and an amine of the general formula:

$R^6$—NH—$R^7$      III, in which $R^6$ and $R^7$ are as defined above, in the presence of a complex of palladium with a diphosphine of the general formula:

$R^8R^9P$—$[CH_2]_n$—$PR^{10}R^{11}$      IV in which $R^8$ to $R^{11}$ and n are as defined above and with a base.

DETAILED DESCRIPTION OF THE INVENTION

It has been found that halogen compounds of the general formula:

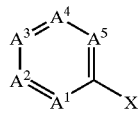

II in which $A^1$ to $A^5$ are as defined above and X is chlorine, bromine or iodine, react directly with carbon monoxide and a primary or secondary amine of the general formula:

$R^6$—NH—$R^7$      III, in which $R^6$ and $R^7$ are as defined above, in the presence of a base, to give good to almost quantitative yields of the desired products (I) if a complex of palladium with a diphosphine of the general formula:

$R^8R^9P$—$[CH_2]_n$—$PR^{10}R^{11}$      IV is present as a catalyst. In the general formula IV, $R^8$ to $R^{11}$ independently of one another are phenyl or substituted phenyl and n is 3 or 4.

Herein, $C_{1-4}$-alkyl is to be understood as meaning any linear or branched primary, secondary or tertiary alkyl group having up to 4 carbon atoms e.g., methyl or ethyl. Herein, aromatic or heteroaromatic radicals are to be understood as meaning especially monocyclic or polycyclic systems, such as, phenyl, naphthyl, biphenylyl, anthracenyl, furyl, pyrrolyl, pyrazolyl, thiophenyl, pyridyl, indolyl or quinolinlyl. These radicals can carry one or more identical or different substituents, for example, lower alkyl groups such as methyl, halogenated alkyl groups such as trifluoromethyl, lower alkoxy groups such as methoxy, or lower alkylthio (alkanesulphanyl) or alkanesulphonyl groups such as methylthio or ethanesulphonyl. Substituted phenyl is understood as meaning especially groups such as (p-)fluorophenyl, (p-)tolyl or (p-)trifluoromethylphenyl.

The halogen compounds (II) used as starting materials are known compounds or can be prepared analogously to known compounds. Numerous compounds of this type have been published, for example, in U.S. Pat. No. 4,254,125 and European Published Patent Application No. 0,001,187.

The halogen compounds (II) in which the group of the formula —OR is bonded to a carbon atom adjacent to a ring nitrogen atom are advantageously prepared by a process in which a dihalide or the general formula:

V

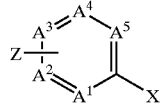

in which $A^1$ to $A^5$ are as defined above, with the proviso that one of the radicals $R^1$ to $R^5$ on a carbon atom adjacent to a ring nitrogen atom is replaced with Z, Z is chlorine, bromine or iodine and X independently thereof is chlorine, bromine or iodine, is reacted with an aromatic or heteroaromatic hydroxyl compound of the general formula:

R—OH      VI, in which R is as defined above. The two-stage process comprising this reaction in combination with the following reaction with carbon monoxide and the amine (III), in the manner described above, is a further subject of the invention; the preferred embodiments described herein and below also are applicable to the two-stage process.

The process according to the invention is preferentially suitable for the preparation of amides (I) in which $A^2$ is nitrogen and forms a pyridine ring with the remaining ring members. Amides (I) in which $R^1$ is a group of the formula —OR, R being as defined above, are particularly preferred.

Other preferred amides (I) are:

those in which $A^1$ is nitrogen and forms a pyridine ring with the remaining ring members, those in which $A^1$ and $A^5$ are nitrogen and form a pyrimidine ring with the remaining ring members, those in which $A^1$ and $A^4$ are nitrogen and form a pyrazine ring with the remaining ring members, and those in which $A^1$, $A^3$ and $A^5$ are nitrogen and form a 1,3,5-triazine ring with the remaining ring members. In the last four classes, those amides in which $R^2$ is a group of the formula —OR, R being as defined above, are in turn particularly preferred. Other preferred amides (I) are those in which R is an optionally substituted phenyl group. This applies especially to the above-mentioned amides containing a pyridine, pyrimidine, pyrazine or 1,3,5-triazine ring in which $R^1$ or $R^2$ is a group of the formula —OR. Other preferred amides are those in which $R^6$ is hydrogen and $R^7$ is an optionally substituted phenyl group.

Preferred halogen compounds (II) are the chlorine compounds (X=Cl).

The catalytically active palladium diphosphine complex is advantageously formed in situ by a process in which palladium in finely divided elemental form (e.g., palladium on activated charcoal), a Pd(II) salt (e.g., the chloride or the acetate) or a suitable Pd(II) complex (e.g., dichlorobis (triphenylphosphine)palladium(II)) is reacted with the diphosphine. The palladium is preferably used in an amount of 0.02 to 0.2 mol percent of Pd(II) or 0.5 to 2 mol percent of Pd(0) (as Pd/C), based in each case on the halogen compound (II). The diphosphine is advantageously used in excess (based on Pd), preferably in an amount of 0.2 to 5 mol percent, again based on the halogen compound (II).

The solvents used can be either relatively nonpolar, for example, toluene or xylene, or polar, for example, acetonitrile, tetrahydrofuran or N,N-dimethylacetamide.

The base used is preferably a relatively weak base, which does not need to be soluble in the solvent used. Examples of suitable bases are carbonates such as sodium carbonate or potassium carbonate, or acetates such as sodium acetate. Particularly good results have been achieved with sodium acetate.

The reaction temperature is preferably 80° to 250° C.

The carbon monoxide pressure is preferably 1 to 50 bar.

The following examples illustrate how the process according to the invention is carried out.

EXAMPLE 1

2-Chloro-6-[3-(trifluoromethyl)phenoxy]pyridine 17.45 g (690 mmol) of sodium hydride (95 percent) was suspended in 420 ml of N,N-dimethylacetamide. 106.7 g (658 mmol) of 3-(trifluoromethyl)phenol was added dropwise over 2 hours at 15° C. The resultant phenate solution was added dropwise over 2.5 hours, under nitrogen, to a solution of 162.4 g (1.097 mol) of 2,6-dichloropyridine in 330 ml of N,N-dimethylacetamide, heated to 90° C. After a further 3 hours of reaction time, the mixture was cooled to room temperature, the precipitate of sodium chloride was filtered off and the filtrate was concentrated. The residue was taken up with toluene and 0.1 N hydrochloric acid, and the organic phase was washed with saturated sodium chloride solution and concentrated. The oily residue (ca. 200 g) was distilled under a vacuum. The yield of the title compound was 151.5 g (84 percent) of a colorless oil, content (GC) 99.8 percent. Other data concerning the title compound was:

$n_D^{20}$=1.5267; MS; m/z: 273/275; 238; 39; $^1$H NMR (CDCl$_3$): δ=6.84 (d, J=7.8 Hz, 1H); 7.07 (d, J=7.8 Hz, 1H); 7.35 (m, 1H); 7.42 (m, 1H); 7.45–7.52 (m, 2H); 7.65 (t, J=7.8 Hz, 1H). $^{13}$C NMR (CDCl$_3$): δ=109.88 (CH); 118.16 (CH); 119.24 (CH); 121.67 (CH); 123.74 (CF$_3$); 124.50 (CH); 130.24 (CH); 132.21 (CCF$_3$); 141.77 (CH); 149.12 (C); 153.89 (C); 162.28 (C).

EXAMPLE 2

3-Chloro-2-[3-(trifluoromethyl)phenoxy]pyridine 20 7.68 g of sodium hydride dispersion (ca. 50 percent in mineral oil) was washed with pentane under nitrogen and 100 ml of N,N-dimethylformamide was then added. 21.92 g (135 mmol) of 3-(trifluoromethyl)phenol was added dropwise over 30 minutes at room temperature. The resultant phenate solution was added dropwise over 2 hours, under nitrogen, to a solution of 20.1 g (136 mmol) of 2,3-dichloropyridine in 80 ml of N,N-dimethylformamide, heated to 120° C. After a reaction time of 3 hours, the mixture was cooled to room temperature, the precipitate of sodium chloride was filtered off and the filtrate was concentrated. The residue was extracted with toluene and 0.1 N hydrochloric acid, and the organic was washed with saturated sodium chloride solution and concentrated. The oily residue was distilled under vacuum. The yield of the title compound was 24.75 g (67 percent) of a colorless oil, content (GC) 99.7 percent. Other data concerning the title compound was:

B.P.$_{18mbar}$=145°–148° C. $n_D^{20}$=1.5282; MS; m/z: 273/275; $^1$H NMR (CDCl$_3$): δ=6.99 (m, 1H); 7.36 (d, 1H); 7.45–7.53 (m, 3H); 7.77 (d, 1H); 8.02 (d, 1H). $^{13}$C NMR (CDCl$_3$): δ=118.66 (CH); 119.44 (C); 119.98 (CH); 121.75 (CH); 123.78 (CF$_3$); 124.94 (CH); 130.13 (CH); 132.16 (CCF$_3$); 139.65 (CH); 145.20 (CH); 153.88 (C); 158.51 (C).

EXAMPLE 3

N-(4-Fluorophenyl)-6-[3-(trifluoromethyl)phenoxy]-pyridine-2-carboxamide 6.84 g (25 mmol) of 2-chloro-6-[3-(trifluoromethyl) phenoxy]pyridine (content 99.5 percent prepared according to Example 1), 4.17 g (37.5 mmol) of 4-fluoroaniline, 2.92 g (27.5 mmol) of sodium carbonate, 0.27 g (0.25 mmol) of palladium/activated charcoal (10 percent Pd) and 0.32 g (0.75 mmol) of 1,4-bis(diphenylphosphino)butane (IV, n=4, $R^8$=$R^9$=$R^{10}$=$R^{11}$=phenyl) in 25 ml of xylene were placed in an autoclave at room temperature. The autoclave was flushed with inert gas, carbon monoxide was then introduced under a pressure of 5 bar and the temperature was raised to 200° C. The CO pressure was increased to 14.5 bar and the mixture was stirred for 16 hours at 200° C. After cooling to room temperature and depressurization, the reaction mixture was treated with 50 ml of xylene and 50 ml of water and filtered. The aqueous phase was extracted with 25 ml of xylene and the combined organic phases were washed with 30 ml of water. The composition of the dissolved products was determined by GC. 92.1 percent of the title compound (amide), 1.9 percent of educt and 6.0 percent of by-products (3.1 percent of secondary amine formed by direct substitution of Cl by the aniline, and 2.9 percent of 2-[3-(trifluoromethyl)phenoxy]pyridine formed by hydrogenolysis) were found. After distillation of the solvent, the crude product (8.63 g) was obtained in the form of a yellow solid. The crude product was purified by recrystallization from methylcyclohexane. the yield of the title compound product was 6.3 g (67 percent) of colorless crystals. The melting point of the product was 104° to 105° C. Other data concerning the title compound was:

MS; m/z: 376 (M$^+$), 238; $^1$H NMR (CDCl$_3$): δ=6.99–7.04 (m, 2H); 7.17 (d, J=8.4 Hz, 1H); 7.40 (m, 1H); 7.46–7.51 (m, 2H); 7.55–7.63 (m, 3H); 7.93 (t, J=7.8Hz, 1H); 8.03 (d, J=7.8 Hz, 1H); 9.24 (br. m, 1 H).

EXAMPLE 4

N-(4-Fluorophenyl)-6-[3-(trifluoromethyl)phenoxy]-pyridine-2-carboxamide

The procedure was described in Example 3 except that the palladium/activated charcoal was replaced with 17.5 mg (25 μmol) of dichlorobis(triphenylphosphine)-palladium(II). The CO pressure was 12.8 bar, the temperature was 150° C. and the reaction time was 17.7 hours. The composition of the dissolved products in the xylene phase was determined by GC. 96.0 percent of the title compound (amide) and 4.0 percent of by-products (2.3 percent of secondary amine, and 1.7 percent of hydrogenolysis product) were found.

EXAMPLE 5

N-(4-Fluorophenyl)-6-[3-(trifluoromethyl)phenoxy]-pyridine-2-carboxamide

The procedure was as described in Example 4 except that the 1,4-bis(diphenylphosphino)butane was replaced with the same molar amount of 1,3-bis(diphenylphosphino)propane (IV, n=3, R$^8$=R$^9$=R$^{10}$=R$^{11}$=phenyl). The CO pressure was 16 bar and the reaction time was 21.6 hours. The composition of the dissolved products in the xylene phase was determined by GC. 98.9 percent of the title compound (amide), 0.1 percent of educt and 1.0 percent of byproducts (0.3 percent of secondary amine and 0.7 percent of hydrogenolysis product) were found.

EXAMPLE 6

N-(2,4-Difluorophenyl)-2-[3-(trifluoromethyl) phenoxy]-pyridine-3-carboxamide(Diflufenicam)

Analogously to Example 4, 6.84 g (25 mmol) of 3-chloro-2-(3-trifluoromethyl)phenoxypyridine (prepared according to Example 2), 4.84 g (37.5 mmol) of 2,4-difluoroaniline, 2.92 g (27.5 mmol) of sodium carbonate, 17.5 mg (25 μmol) of dichlorobis(triphenylphosphine)-palladium(II) and 0.32 g (0.75 mmol) of 1,4-bis(diphenylphosphino)butane in 25 ml of xylene were reacted under a CO pressure of 15 bar at 190° to 195° C. for 19 hours. The conversion was ca. 80 percent. The mixture was worked up as in Example 3 to give 6 g of crude product in the form of a yellow crystalline solid. It was purified by recrystallization from 50 ml of methylcyclohexane. The yield of the title compound was 3.25 g (33 percent) of a white solid. The melting point of the title compound was 157° to 159° C. Other data concerning the title compound was:

MS; m/z: 394 (M$^+$), 266 (100%); $^1$H NMR (CDCl$_3$): δ=6.89–6.96 (m, 2H); 7.26 (m, 1 H); 7.46 (m, 1H); 7.54–7.63 (m, 3H); 8.28 (dd, 1H); 8.52 (m, 1H); 8.71 (dd, 1H); 9.97 (br. s, 1H).

COMPARATIVE EXAMPLE 1

The procedure was as described in Example 4 except that the 1,4-bis(diphenylphosphino)butane was replaced with the same molar amount of triphenylphosphine. After a reaction time of 15.5 hours at a CO pressure of 15 bar, the composition of the dissolved products in the xylene phase was determined by GC. Only 43.2 percent of the desired product and 56.8 percent of unconverted educt were found.

COMPARATIVE EXAMPLE 2

The procedure was as described in Example 4 except that the 1,4-bis(diphenylphosphino)butane was replaced with the same molar amount of tri-n-butylphosphine. After a reaction time of 15 hours at a CO pressure of 14 bar, the composition of the dissolved products in the xylene phase was determined by GC. Only traces (0.4 percent) of the desired product and 96.8 percent of unconverted educt were found.

COMPARATIVE EXAMPLE 3

The procedure was as described in Example 4 except that the 1,4-bis(diphenylphosphino)butane was replaced with the same molar amount of 1,2-bis(diphenylphosphino)ethane. After a reaction time of 20.2 hours at a CO pressure of 14.7 bar, the composition of the dissolved products in the xylene phase was determined by GC. Only traces (2.2 percent) of the desired product and 97.7 percent of unconverted educt were found.

What is claimed is:

1. A process for the preparation of an amide of formula:

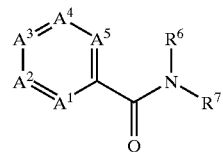

wherein:

$A^1$ is nitrogen or $CR^1$, $A^2$ is nitrogen or $CR^2$, $A^3$ is nitrogen or $CR^3$, $A^4$ is nitrogen or $CR^4$, and $A^5$ is nitrogen or $CR^5$, with the proviso that at least one of the ring members is $A^1$ to $A^5$ is nitrogen and that two nitrogen atoms are not bonded directly to one another;

$R^1$ to $R^5$, if present, independently of one another are each a member of the group consisting of hydrogen, $C_{1-4}$-alkyl or aryl, also one of the substituents $R^1$ to $R^5$ being a group of the formula —OR, in which R is an aromatic radical, a heteroaromatic radical, an aromatic radical substituted with at least one lower alkyl, halogenated alkyl, lower alkoxy, lower alkylthio or alkanesulfonyl, or (p-) fluorophenyl, or a heteroaromatic radical substituted with at least one lower alkyl, halogenated alkyl, lower alkoxy, lower alkylthio or alkanesulfonyl;

$R^6$ is hydrogen or $C_{1-4}$-alkyl; and $R^7$ is an aromatic radical, a heteroaromatic radical, an aromatic radical substituted with at least one lower alkyl, halogenated alkyl, lower alkoxy, lower alkylthio or alkanesulfonyl, or (p-) fluorophenyl, or a heteroaromatic radical substituted with at least one lower alkyl, halogenated alkyl, lower alkoxy, lower alkylthio or alkanesulfonyl.

in a first step, reacting a dihalide of the formula:

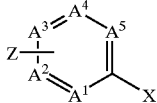
V wherein $A^1$ to $A^5$ are as defined above, with the proviso that one of the radicals $R^1$ to $R^5$ on a carbon atom adjacent to a ring nitrogen atom is replaced with Z, Z is chlorine, bromine or iodine, and X independently thereof is chlorine, bromine or iodine, with an aromatic or heteroaromatic hydroxyl compound of formula:

R—OH    VI, wherein R is as defined above, to give a (hetero)aryloxy halogen compound of formula:

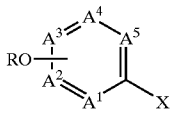
II' wherein $A^1$ to $A^5$, and X are as defined above, and, in a second step, said product is reacted with carbon monoxide and an amine of formula:

$R^6$—NH—$R^7$    III wherein $R^6$ and $R^7$ are as defined above, in the presence of a complex of palladium with a diphosphine of formula:

$R^8R^9P$—$[CH_2]_n$—$PR^{10}R^{11}$    IV wherein $R^8$ to $R^{11}$ independently of one another are each phenyl or substituted phenyl, and n is 3 or 4, with a base other than said primary or secondary amine.

2. A process for the preparation of an amide of formula:

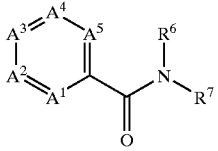
I wherein:
  $A^1$ is nitrogen or $CR^1$,
  $A^2$ is nitrogen or $CR^2$,
  $A^3$ is nitrogen or $CR^3$,
  $A^4$ is nitrogen or $CR^4$, and
  $A^5$ is nitrogen or $CR^5$,
    with the proviso that at least one of the ring members $A^1$ to $A^5$ is nitrogen and that two nitrogen atoms are not bonded directly to one another;
  $R^1$ to $R^5$, if present, independently of one another are each a member selected from the group consisting of hydrogen, $C_{1-4}$-alkyl and aryl, also one of the substituents $R^1$ to $R^5$ being a group of the formula —OR, in which R is an aromatic radical, a heteroaromatic radical, an aromatic radical substituted with at least one member being selected from the group consisting of lower alkyl, halogenated alkyl lower alkoxy, lower alkylthio and alkanesulfonyl, or (p-)fluorophenyl, or a heteroaromatic radical substituted with at least one member being selected from the group consisting of lower alkyl, halogenated alkyl, lower alkoxy, lower alkylthio or alkanesulfonyl;
  $R^6$ is hydrogen or $C_{1-4}$-alkyl; and
  $R^7$ is an aromatic radical, a heteroaromatic radical, an aromatic radical substituted with at least one member selected from the group consisting of lower alkyl, halogenated alkyl, lower alkoxy, lower alkylthio and alkanesulfonyl, or (p-)fluorophenyl, or a heteroaromatic radical substituted with at least one member being selected from the group consisting of lower alkyl, halogenated alkyl, lower alkoxy, lower alkylthio and alkanesulfonyl, comprising reacting a halogen compound of the formula:

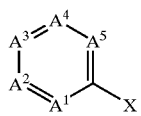
II wherein $A^1$ to $A^5$ are as defined above and X is chlorine, bromine or iodine, with carbon monoxide and a primary or secondary amine of the formula:

$R^6$—NH—$R^7$    III wherein $R^6$ and $R^7$ are as defined above, in the presence of a complex of palladium with a diphosphine of the formula:

$R^8R^9P$—$[CH_2]_n$—$PR^{10}R^{11}$    IV, in which $R^8$ and $R^{11}$ independently of one another are each phenyl or substituted phenyl, and n is 3 or 4, and with a base other than said primary or secondary amine.

3. The process according to claim 2, wherein $A^2$ is nitrogen and part of a pyridine ring.

4. The process according to claim 3, wherein $R^1$ is a group of the formula —OR.

5. The process according to claim 2, wherein $A^1$ is nitrogen and part of a pyridine ring.

6. The process according to claim 2, wherein $A^1$ and $A^5$ are nitrogen and part of a pyrimidine ring.

7. The process according to claim 2, wherein $A^1$ and $A^4$ are nitrogen and part of a pyrazine ring.

8. The process according to claim 2, wherein $A^1$, $A^3$ and $A^5$ are nitrogen.

9. The process according to claim 8, wherein $R^2$ is a group of the formula —OR.

10. The process according to claim 9, wherein R is an optionally substituted phenyl group.

11. The process according to claim 5, wherein $R^2$ is a group of the formula —OR.

12. The process according to claim 6, wherein $R^2$ is a group of the formula —OR.

13. The process according to claim 7, wherein $R^2$ is a group of the formula —OR.

14. The process according to claim 2, wherein $A^1$ is $CR^1$ and $R^1$ is a group of the formula —OR.

15. The process according to claim 14, wherein R is an optionally substituted phenyl group.

16. The process according to claim 2, wherein $R^6$ is hydrogen and $R^7$ is an optionally substituted phenyl group.

17. The process according to claim 2, wherein X is chlorine.

18. The process according to claim 2, wherein the diphosphine (IV) used is 1,3-bis(diphenylphosphino)propane or 1,4-bis(diphenylphosphino)butane.

* * * * *